(12) United States Patent
Wang et al.

(10) Patent No.: US 9,468,557 B2
(45) Date of Patent: Oct. 18, 2016

(54) COMPACT HEAT EXCHANGER FOR VENO-VENOUS PERFUSION-INDUCED SYSTEMIC HYPERTHERMIA SYSTEMS

(75) Inventors: Dongfang Wang, Lexington, KY (US); Joseph B. Zwischenberger, Lexington, KY (US)

(73) Assignee: THE UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 626 days.

(21) Appl. No.: 13/584,696

(22) Filed: Aug. 13, 2012

(65) Prior Publication Data

US 2013/0211483 A1    Aug. 15, 2013

Related U.S. Application Data

(60) Provisional application No. 61/522,411, filed on Aug. 11, 2011, provisional application No. 61/651,164, filed on May 24, 2012.

(51) Int. Cl.
*A61F 7/00* (2006.01)
*A61M 1/26* (2006.01)
*A61M 1/16* (2006.01)
*A61M 1/10* (2006.01)

(52) U.S. Cl.
CPC .......... *A61F 7/0085* (2013.01); *A61M 1/1698* (2013.01); *A61M 1/26* (2013.01); *A61M 2001/1006* (2013.01); *A61M 2001/1065* (2013.01); *A61M 2001/267* (2013.01)

(58) Field of Classification Search
CPC .............. A61F 2007/126; A61F 2007/0054; A61F 7/12; A61M 1/16; A61M 1/3666

USPC .......... 607/104–106; 600/18; 604/6.13, 4.01
See application file for complete search history.

(56) References Cited

U.S. PATENT DOCUMENTS

| 973,868 | A | 10/1910 | Kneuper |
|---|---|---|---|
| 2,474,665 | A | 6/1949 | Guarino |
| 2,742,158 | A | 4/1956 | Schuller |
| 3,103,928 | A | 9/1963 | Broman |
| 3,183,908 | A | 5/1965 | Collins et al. |
| 3,410,263 | A | 11/1968 | McGinnis |
| 3,429,443 | A | 2/1969 | Stern |

(Continued)

OTHER PUBLICATIONS

United States Patent and Trademark Office, U.S. Appl. No. 13/584,704, Office Action dated Mar. 11, 2014, 9 pages.

(Continued)

*Primary Examiner* — Kaitlyn Smith
*Assistant Examiner* — Yasamin Ekrami
(74) *Attorney, Agent, or Firm* — King & Schickli, PLLC

(57) ABSTRACT

A compact heat exchanger for veno-venous perfusion-induced hyperthermia includes an integral pneumatic pump and a hollow tubule heat exchange array. A veno-venous perfusion-induced hyperthermia system incorporating the compact heat exchanger is described. The heat exchanger provides a compact, efficient design allowing a lesser heat exchanging surface area and lesser required pumping power compared to conventional systems. In turn, the system provides a shorter blood circuit compared to conventional systems, allowing maintaining a lower blood temperature than such conventional systems while supplying sufficiently heated blood to patient visceral organs to provide a therapeutic effect, such as in supplementing chemotherapy drugs.

11 Claims, 7 Drawing Sheets

(56) References Cited

U.S. PATENT DOCUMENTS

| | | |
|---|---|---|
| 3,768,977 A | 10/1973 | Brumfield et al. |
| 3,855,995 A | 12/1974 | Bentley |
| 3,856,475 A | 12/1974 | Marx |
| 3,898,045 A | 8/1975 | Bowley |
| 3,934,982 A | 1/1976 | Arp |
| 3,935,110 A | 1/1976 | Schmid et al. |
| 3,960,657 A | 6/1976 | Bowley |
| 3,989,626 A | 11/1976 | Bentley et al. |
| 4,017,279 A | 4/1977 | Bowley |
| 4,094,792 A | 6/1978 | Bentley |
| 4,098,275 A | 7/1978 | Consalvo |
| 4,134,402 A | 1/1979 | Mahurkar |
| 4,188,360 A | 2/1980 | Kurata |
| 4,196,075 A | 4/1980 | Bentley |
| 4,205,042 A | 5/1980 | Lobdell et al. |
| 4,268,476 A | 5/1981 | Raible |
| 4,297,318 A | 10/1981 | Raible |
| 4,368,118 A | 1/1983 | Siposs |
| 4,372,914 A | 2/1983 | Raible |
| 4,374,088 A | 2/1983 | Stenberg et al. |
| 4,533,516 A | 8/1985 | Johnsson et al. |
| 4,552,552 A | 11/1985 | Polaschegg et al. |
| 4,573,883 A | 3/1986 | Noon et al. |
| 4,612,126 A | 9/1986 | Alt et al. |
| 4,623,518 A | 11/1986 | Raible |
| 4,698,207 A | 10/1987 | Bringham et al. |
| 4,770,652 A | 9/1988 | Mahurkar |
| 4,808,155 A | 2/1989 | Mahurkar |
| 4,874,581 A | 10/1989 | Sutherland et al. |
| 4,906,229 A | 3/1990 | Wampler |
| 4,908,014 A | 3/1990 | Kroyer |
| 4,915,837 A | 4/1990 | Verity |
| 4,925,377 A | 5/1990 | Inacio et al. |
| 4,975,247 A | 12/1990 | Badolato et al. |
| 5,034,188 A | 7/1991 | Nakanishi et al. |
| 5,058,661 A * | 10/1991 | Oshiyama ............... A61M 5/44 165/11.1 |
| RE33,932 E | 5/1992 | Fukasawa et al. |
| 5,116,308 A | 5/1992 | Hagiwara |
| 5,120,501 A | 6/1992 | Mathewson et al. |
| 5,139,741 A | 8/1992 | Hagiwara |
| 5,158,533 A | 10/1992 | Strauss et al. |
| 5,188,732 A | 2/1993 | De Niel et al. |
| 5,197,951 A | 3/1993 | Mahurkar |
| 5,217,689 A | 6/1993 | Raible |
| 5,221,255 A | 6/1993 | Mahurkar et al. |
| 5,225,161 A | 7/1993 | Mathewson et al. |
| 5,236,665 A | 8/1993 | Mathewson et al. |
| 5,270,004 A | 12/1993 | Cosentino et al. |
| 5,270,005 A | 12/1993 | Raible |
| 5,282,783 A | 2/1994 | Lindsay |
| 5,316,724 A | 5/1994 | Mathewson et al. |
| 5,338,512 A | 8/1994 | Mathewson et al. |
| 5,354,277 A | 10/1994 | Guzman et al. |
| 5,358,689 A | 10/1994 | Jones et al. |
| 5,374,245 A | 12/1994 | Mahurkar |
| 5,395,525 A | 3/1995 | Takano et al. |
| 5,421,405 A | 6/1995 | Goodin et al. |
| 5,476,444 A | 12/1995 | Keeling et al. |
| 5,718,871 A | 2/1998 | Elgas |
| 5,762,868 A | 6/1998 | Leonard |
| 5,762,875 A | 6/1998 | Gremel et al. |
| 5,770,149 A | 6/1998 | Raible |
| 5,787,729 A | 8/1998 | Wijaya |
| 5,788,287 A | 8/1998 | Gremel |
| 5,817,279 A | 10/1998 | Eilers et al. |
| 5,823,987 A * | 10/1998 | Elgas et al. ............... 604/6.13 |
| 5,858,233 A | 1/1999 | Elgas et al. |
| 5,906,741 A | 5/1999 | Elgas et al. |
| 5,922,202 A | 7/1999 | Elgas et al. |
| 5,958,255 A | 9/1999 | Hobrecht et al. |
| 6,017,493 A | 1/2000 | Cambron et al. |
| 6,224,829 B1 | 5/2001 | Piplani et al. |
| 6,336,911 B1 | 1/2002 | Westerbeck |
| 6,368,557 B1 | 4/2002 | Piplani et al. |
| 6,379,618 B1 | 4/2002 | Piplani et al. |
| 6,395,226 B1 | 5/2002 | Plunkett |
| 6,406,452 B1 | 6/2002 | Westerbeck |
| 6,413,233 B1 | 7/2002 | Sites et al. |
| 6,428,747 B1 | 8/2002 | Dueri et al. |
| 6,454,999 B1 | 9/2002 | Farhangnia et al. |
| 6,497,841 B1 | 12/2002 | Plotkin et al. |
| 6,503,450 B1 | 1/2003 | Afzal et al. |
| 6,508,983 B1 | 1/2003 | McBurney et al. |
| 6,572,821 B2 | 6/2003 | Knott |
| 6,579,496 B1 | 6/2003 | Fausset et al. |
| 6,607,517 B1 * | 8/2003 | Dae et al. ............... 604/500 |
| 6,613,008 B2 * | 9/2003 | Aboul-Hosn et al. ....... 604/5.01 |
| 6,630,107 B1 | 10/2003 | Merce Vives |
| 6,644,320 B2 | 11/2003 | Groth et al. |
| 6,669,661 B1 | 12/2003 | Yee |
| 6,682,698 B2 | 1/2004 | Chambers et al. |
| 6,689,315 B2 | 2/2004 | Linker et al. |
| 6,716,157 B2 | 4/2004 | Goldowsky |
| 6,716,188 B2 | 4/2004 | Noda et al. |
| 6,723,283 B2 | 4/2004 | Ghelli et al. |
| 6,726,653 B2 | 4/2004 | Noda et al. |
| 6,730,267 B2 | 5/2004 | Stringer et al. |
| 6,884,360 B2 | 4/2005 | Chang |
| 6,908,446 B2 | 6/2005 | Yokoyama et al. |
| 6,960,322 B2 | 11/2005 | Stringer et al. |
| 7,022,099 B2 | 4/2006 | Litzie et al. |
| 7,022,284 B2 | 4/2006 | Brian et al. |
| 7,135,008 B2 | 11/2006 | O'Mahony et al. |
| 7,238,320 B2 | 7/2007 | Ghelli et al. |
| 7,541,000 B2 | 6/2009 | Stringer et al. |
| 7,785,247 B2 | 8/2010 | Tatum et al. |
| 7,819,835 B2 * | 10/2010 | Landy et al. ............... 604/6.13 |
| 2002/0044889 A1 * | 4/2002 | Aboul-Hosn ....... A61M 1/1698 422/45 |
| 2004/0226868 A1 | 11/2004 | Shoji et al. |
| 2006/0009728 A1 | 1/2006 | Litzie et al. |
| 2006/0177343 A1 | 8/2006 | Brian, III et al. |
| 2007/0217948 A1 | 9/2007 | Ghelli et al. |
| 2007/0249888 A1 | 10/2007 | Wu et al. |
| 2008/0199357 A1 | 8/2008 | Gellman et al. |
| 2008/0234623 A1 | 9/2008 | Strauss et al. |
| 2009/0087342 A1 * | 4/2009 | Maianti ............... A61M 1/1698 422/46 |
| 2010/0106072 A1 | 4/2010 | Kashefi-Korasani et al. |
| 2010/0274170 A1 * | 10/2010 | Carpenter et al. ........... 604/6.09 |
| 2013/0004369 A1 | 1/2013 | Marseille |

OTHER PUBLICATIONS

United States Patent and Trademark Office, U.S. Appl. No. 13/584,704, Office Action dated Jun. 25, 2014, 8 pages.

United States Patent and Trademark Office, U.S. Appl. No. 13/584,704, Notice of Allowance and Fee(s) Due, dated Aug. 22, 2014, 7 pages.

* cited by examiner

COMPACT HEAT EXCHANGER FOR VENO-VENOUS PERFUSION-INDUCED SYSTEMIC HYPERTHERMIA SYSTEMS

This application claims the benefit of priority in U.S. Provisional Patent Application Ser. Nos. 61/522,411 filed on Aug. 11, 2011 and 61/651,164 filed on May 24, 2012, the entirety of the disclosures of each of which are incorporated herein by reference.

TECHNICAL FIELD

The present invention relates generally to the field of medical devices. In particular, the invention relates to a compact heat exchanger for use in veno-venous perfusion induced systemic hyperthermia (vv-PISH) systems.

BACKGROUND OF THE INVENTION

In 2007 lung cancer was responsible for 31% of all cancer-related deaths. Advanced stage NSCLC present in 75% of all new lung cancer cases provides a median survival rate of only 9-12 months despite maximal combination chemotherapy. Despite improvements in cancer therapies, the long-term prognosis for patients with metastatic lung cancer remains dismal, and indeed chemotherapy provides only a modest improvement in survival over supportive care alone.

It has been shown that regional and local hyperthermia exhibits synergism with various conventional chemotherapy agents. Hyperthermia selectively kills cancer cells and enhances cytotoxicity of certain chemotherapy drugs, increases tumor blood flow and permeability of tumor blood vessels, and thereby increases drug delivery into a tumor. For example, hyperthermia enhances platinum uptake and inhibits platinum-induce DNA adduct repair, an effect that may be important in reversing cisplatin resistance. Thus, concurrent combined hyperthermia and chemotherapy has great potential in advanced NCSCLC therapy.

Because advanced stage NSCLC patients often have metastasis to remote sites, it is contemplated that systemic hyperthermia would provide advantages over local hyperthermia. Systemic hyperthermia causes marked physiological changes, but damage to normal tissue occurs when temperatures exceed 44 C. Heat has a selective killing effect on malignant phenotypes (lung, colon, and pancreatic cancers, for example) at temperatures between those exhibited during normal fevers and temperatures that induce tissue destruction (41-45 C). This suggests that a hyperthermia therapeutic window may exist for cancer therapy. However, conventional heat delivery such as radiant heat disadvantageously redistributes blood flow away from visceral organs to skin, and peripheral tissue, resulting in heterogenous heat distribution. This leads to insufficient heat delivery to provide a therapeutic benefit, compromising treatment efficiency, and also induces pain and peripheral nerve damage. In turn, conventional veno-venous perfusion-induced hyperthermia systems, because of their relatively long tubing lengths and requiring multiple cannulations (increased circuit lengths), must heat blood to unacceptable temperatures (46 C and above) to provide the desired hyperthermic effect, risking damage to blood cells and pain to the patient.

To solve this and other problems, the present disclosure provides a veno-venous perfusion-induced hyperthermia system (vv-PISH) which delivers more heat to visceral organs for metastatic cancer treatment while eliminating complications and disadvantages of radiant heat. The system includes, a compact heat exchanger including an integral pneumatic pump and blood flow redirector structures. The device of the present disclosure provides an even blood flow pattern, preventing or reducing incidence of thrombosis. In turn, the presently disclosed design simplifies the blood circuit and also provides a pulsatile blood flow pattern, promoting active blood mixing and thereby improving gas exchange within the pump. The present device finds use at least as a supplemental therapy for conventional chemotherapy regimens.

SUMMARY OF THE INVENTION

The present disclosure provides a blood heat exchanger for use as a supplement or replacement therapeutic treatment to conventional chemotherapy. The heat exchanger includes an integral pneumatic pump enclosed substantially within a housing thereof, providing a compact and efficient design. Inlet blood redirectors and outlet blood collectors are provided, which in combination with the integral pneumatic pump promote an even perfusion and mixing of blood, eliminating areas of stagnation and improving heat exchange.

In an embodiment, an atrium is provided at an inlet of the blood heat exchanger. The atrium is defined by one or more additional pneumatic pumps for promoting blood flow from a patient body into the heat exchanger. By cyclically maintaining an internal pressure of the atrium pneumatic pump(s) at zero or less, a constant, even supply of blood from the patient is provided at the blood heat exchanger inlet, thereby eliminating the pulsatile inlet blood flow patterns provided by conventional pumping systems.

In turn, a veno-venous perfusion-induced systemic hyperthermia system (vv-PISH) incorporating the heat exchanger of the present disclosure is described, for removing cooler blood from a patient body and returning heated blood to same.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims. Unless otherwise indicated, any references discussed herein are specifically incorporated by reference in their entirety into the present disclosure.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE
ILLUSTRATED EMBODIMENTS

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention. Also, it is to be understood that other embodiments may be utilized and that process, reagent, software, and/or other changes may be made without departing from the scope of the present invention.

Figure 1:
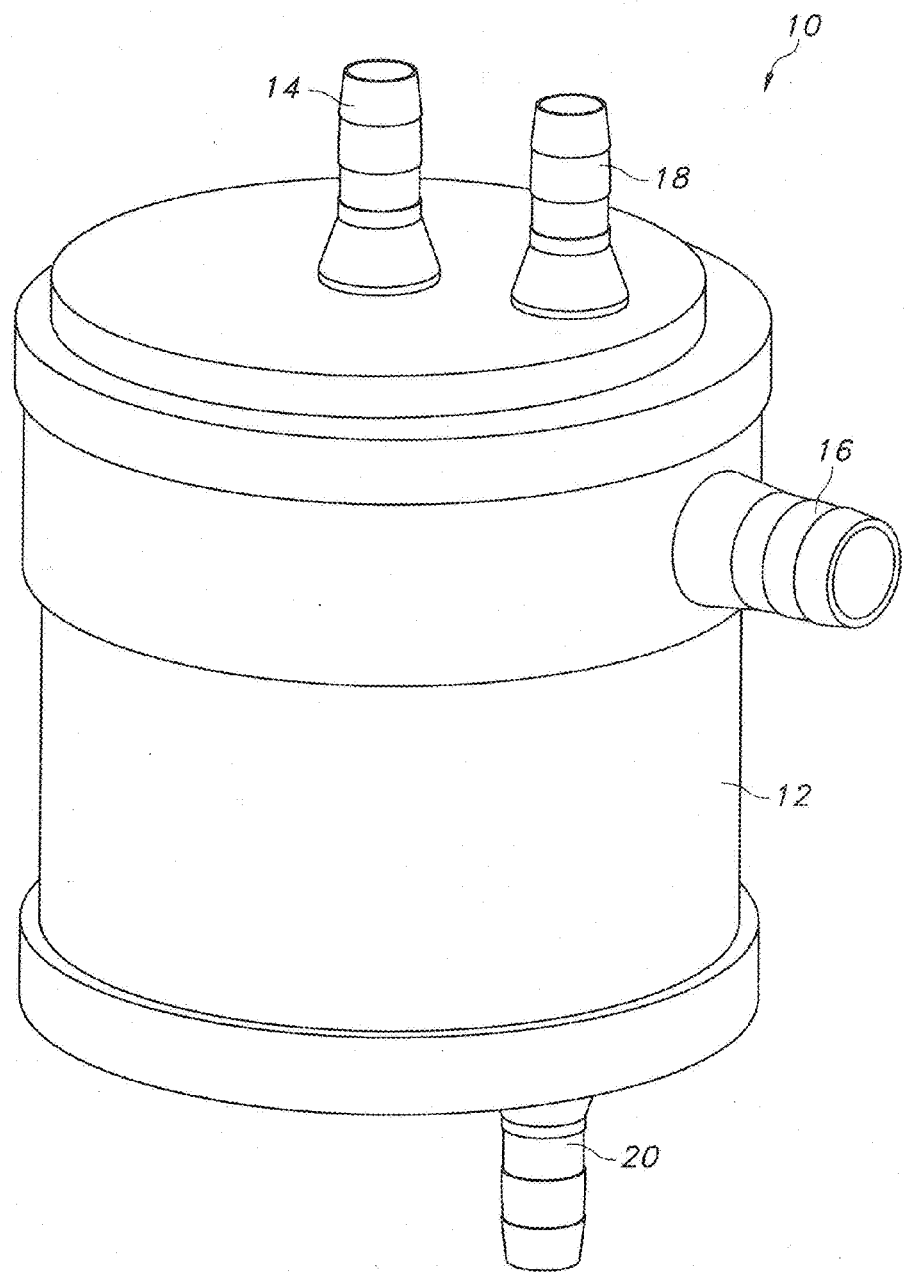
FIG. 1 shows a housing for the heat exchanger of the present disclosure.

In one aspect, the present disclosure provides a compact heat exchanger 10 (see FIG. 1) including a housing 12, at least one blood inlet 14, and at least one blood outlet 16. At least one heated fluid inlet 18 and at least one heated fluid outlet 20 are provided for supplying a heated fluid to and removing same from the heat exchanger 10, typically with the heated fluid being passed through a hollow heat exchanging tubule array 22 of the heat exchanger 10 in a counter-current direction compared to that of the blood flow. The heat exchanging tubule array 22 may be fabricated of any suitable heat exchanging metal. In an embodiment, the tubules of the heat exchanging tubule array 22 are fabricated of 0.2 mm thick stainless steel tubing and provide approximately 0.095-0.113 $m^2$ of total heat exchanging surface.

Figure 2:
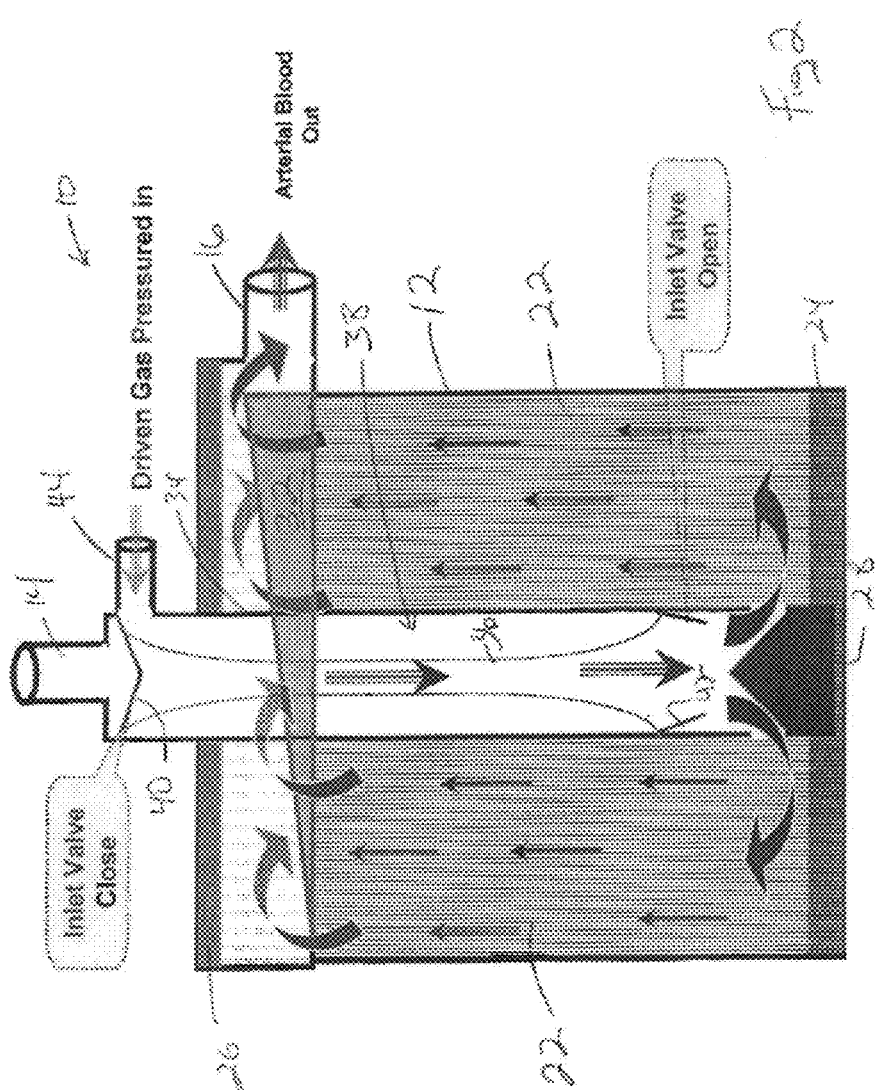
FIG. 2 shows a cross-sectional side view of the heat exchanger

As shown in FIG. 2, arrays 22 of heat exchanging tubules may be provided arranged substantially parallel to a longitudinal axis of the heat exchanger 10 housing 12, or alternatively diagonal spirally wound heat exchanging tubule arrays 22 (not shown) may be provided. Inlet potting 24 and outlet potting 26, known in the art, is provided and disposed to prevent entry of blood into the lumens of the hollow heat exchanging tubules of the heat exchanging tubule array 22 and direct mixing with the heated fluid contained therein. The inlet potting 24 may define an inverted dome shape, further assisting in promoting even redistribution of blood passing through the heat exchanger 10. The inlet potting 24 may define an inverted dome shape, further assisting in promoting even redistribution of blood passing through the heat exchanger 10.

Figure 3:
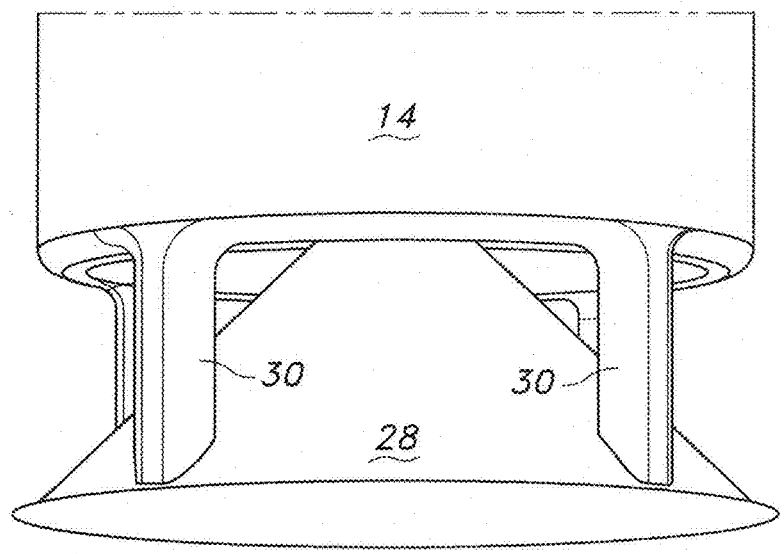
FIG. 3 shows an inlet blood flow redirector for the heat exchanger.

The system 10 of the invention further includes blood flow redirector structures, providing an even blood flow pattern as blood passes through the heat exchanger 10. An inlet blood flow redirector 28 is provided at an end of the heat exchanger 10 distal from the blood inlet 14 for evenly redirecting blood flow passing through the blood inlet 14. In an embodiment, a frusto-conical inlet blood flow redirector 28 is provided at a distal end of the blood inlet 14 (see FIG. 3), secured to or molded with the distal end of the blood inlet 14 by one or more columns 30. At least a portion of the conical inlet blood flow redirector 28 is disposed in an interior of the blood inlet 14 distal end. Like structures are described in U.S. Pat. No. 8,906,300, filed concurrently herewith and incorporated herein in its entirety by reference. As shown in FIG. 2, the inlet blood flow redirector 28 promotes even radial perfusion across a surface of the inlet potting 24 at a bottom of the heat exchanger and also even axial blood flow as blood travels through the heat exchanger 10 towards the blood outlet 16 (see arrows), eliminating stagnant blood flow in the heat exchanger 10. In turn, a blood collection channel 32 is provided at a top of the heat exchanger 10, whereby blood exiting the heat exchanging tubule array 22 is collected and redirected to the blood outlet 16 (see FIGS. 2 and 4). A substantially crescent-shaped blood collection channel 32 is shown, although the skilled artisan will appreciate that other cross-sectional shapes are possible and contemplated, such as segmental, triangular, etc. The blood collection channel 32 regulates blood flow evenly at the outlet end of the heat exchanger 10, and further guides blood to the blood outlet 16. That is, blood enters via the blood inlet 14 and is evenly redirected by the inlet blood flow redirector 28 as summarized above to pass over the heat exchanging tubule array 22. On exiting the heat exchanging tubule array 22, blood passes into the blood collection channel 32 and therefrom exits the heat exchanger 10 via the blood outlet 16. In that manner, areas of stagnant blood flow at or near the blood outlet 16 are reduced or eliminated.

Figure 4:
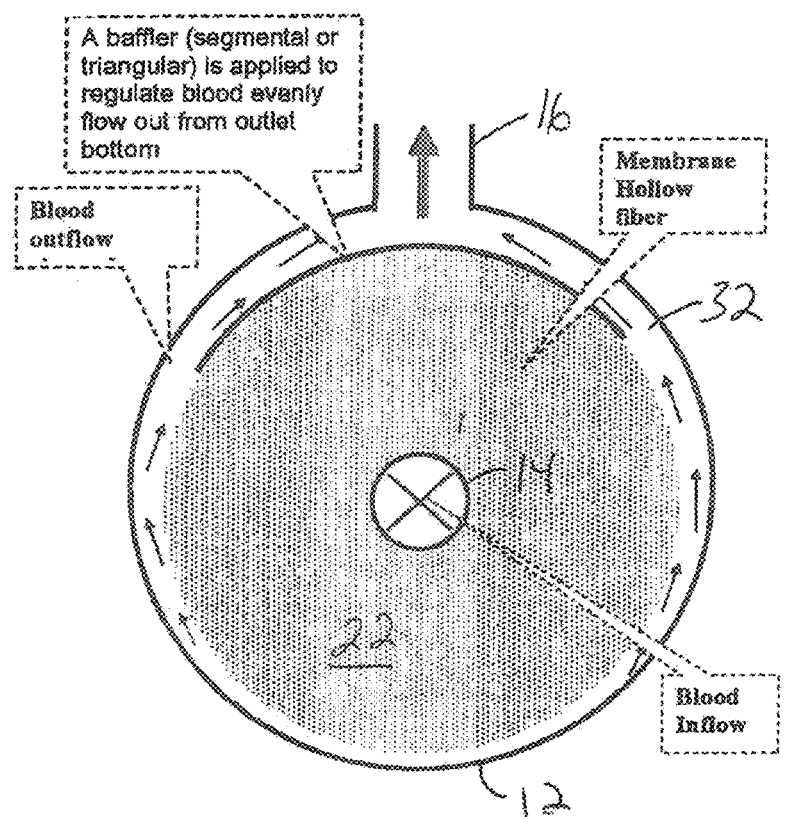
FIG. 4 shows a top view of the heat exchanger of the disclosure.

In turn, a blood collection channel 32 is provided at a top of the heat exchanger 10, whereby blood exiting the heat exchanging tubule array 22 is collected and redirected to the blood outlet 16 (see FIGS. 2 and 4). A substantially crescent-shaped blood collection channel 32 is shown, although the skilled artisan will appreciate that other cross-sectional shapes are possible and contemplated, such as segmental, triangular, ect. The blood collection channel 32 regulates blood flow evenly at the outlet end of the heat exchanger 10, and further guides blood to the blood outlet 16. That is, blood enters via the blood inlet 14 and is evenly redirected by the inlet blood flow redirector 28 as summarized above to pass over the heat exchanging tubule array 22. On exiting the heat exchanging tubule array 22, blood passes into the blood collection channel 32 and therefrom exits the heat exchanger 10 via the blood outlet 16. In manner, areas of stagnant blood flow at or near the blood outlet 16 are reduced or eliminated.

Rather than utilizing an external pump as is common with conventional heat exchangers, the heat exchanger 10 of the present disclosure includes an integral pneumatic pump to provide pumping action for passing blood from the blood inlet 14, over the heat exchanging tubule array 22, and to the blood outlet 16. As such, a compact, economical and efficient combination of pump and heat exchanger is provided. Providing further advantages, the integral pneumatic pump provides a pulsatile blood flow pattern, promoting active blood mixing as the blood passes through the heat exchanger 10, for improved heat exchange performance and an improved blood flow pattern to reduce thrombogenicity. Because of that improved gas exchange performance, it is possible to provide a lesser heat exchange surface area compared to conventional heat exchangers, allowing a more compact unit.

Figure 5:
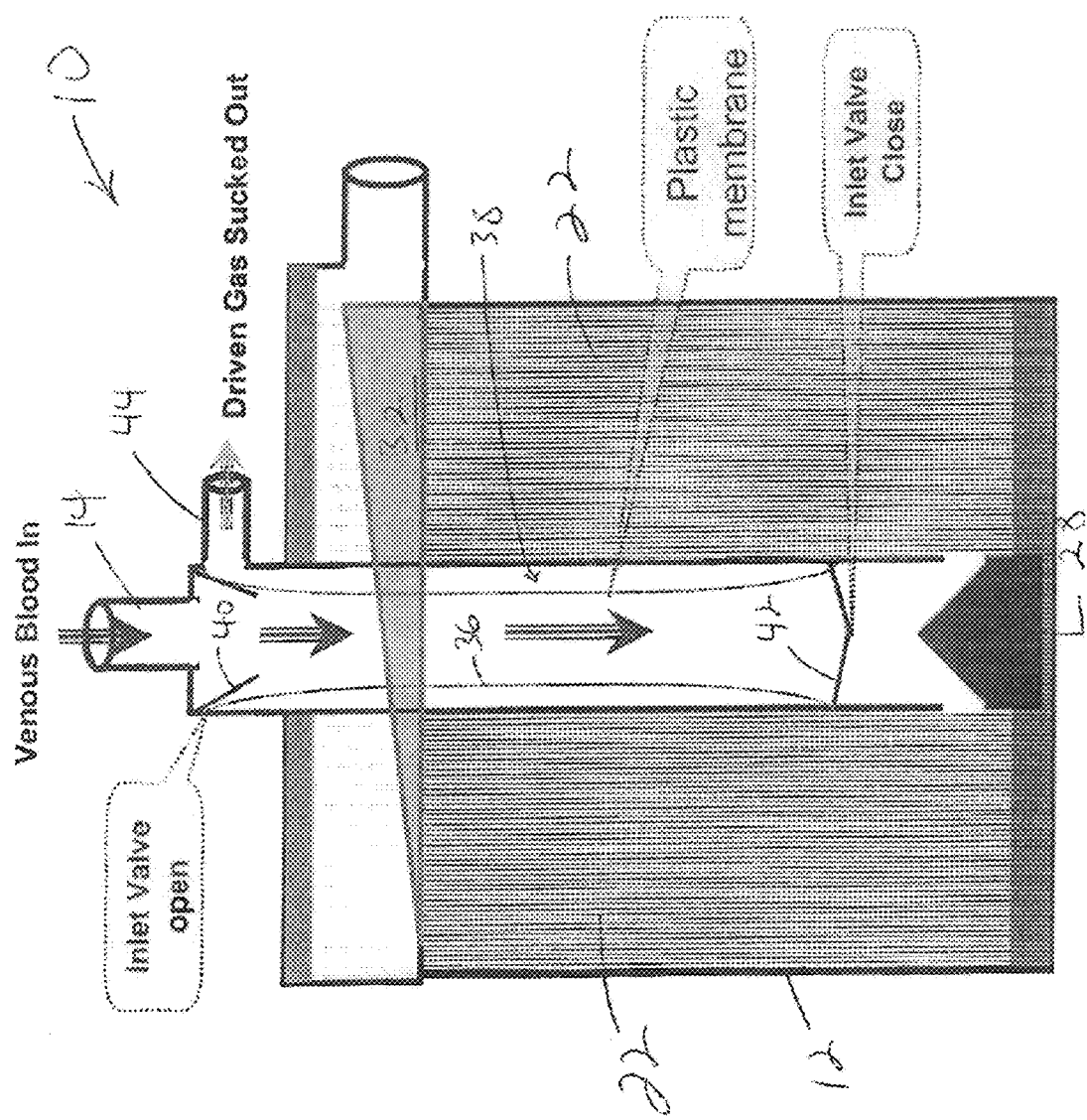
FIG. 5 shows a cross-sectional side view of the heat exchanger, including an integrated pneumatic pump.

With reference to FIG. 5, a cylinder 34 is disposed in an interior of the heat exchanging tubule array 22, Within cylinder 34, a flexible membrane 36 is disposed to define a pneumatic pump 38. Pump inlet and outlet valves 40, 42, in an embodiment being duck-bill valves of known configuration, prevent other than a uni-directional blood flow through the pneumatic pump 38 (see arrows).

A pump gas inlet/outlet 44 is connected to a pneumatic console (not shown) for providing gas to operate the pneumatic pump 38. Pump gas is cyclically supplied to and withdrawn from the pump gas inlet/outlet 44, causing the flexible membrane 36 to expand and contract, providing a pumping action to promote blood flow. As shown in FIGS. 2 and 5, when gas is supplied to the pump gas inlet/outlet 44

(systole), the flexible membrane 36 collapses, closing the pump inlet valve 40 and forcing blood out of the pneumatic pump 38 via the now open outlet valve 42 to pass over the heat exchanging tubule array 22. When gas is withdrawn from the pump gas inlet/outlet 44 (diastole), the flexible membrane 36 expands, closing the pump outlet valve 42 and opening the pump inlet valve 40, generating negative pressure and drawing blood into the pneumatic pump 38 from the patient's body through the now-open pump inlet valve 40 (FIG. 5). On the next cycle, the blood is delivered from the pneumatic pump 38 as described above.

In an embodiment, a heat exchanger 10 was fabricated having an integral pneumatic pump 38 with an outer diameter of approximately 20 mm. In bench tests using 37% glycerin in a mock blood flow circuit, this device was shown to provide a pumping rate of from 1.251 L/min at 40 beats per minute to 3.2 L/min at 90 beats per minute against 100 mm Hg afterload, which was more than sufficient to meet a benchmark of 1-1.5 L/min. Heat exchange efficiency for this device was above 70% at a flow rate of 1-1.5 L/min.

By the foregoing design, a heat exchanger 10 is possible which provides a desired circuit blood flow rate of 0.5-2.0 L/min, an therapeutic hyperthermia dose of 42 C for 120 min, a heating period of less than 40 minutes, an infusion blood temperature of 44 C or less, and stable hemodynamics.

Figure 6A:
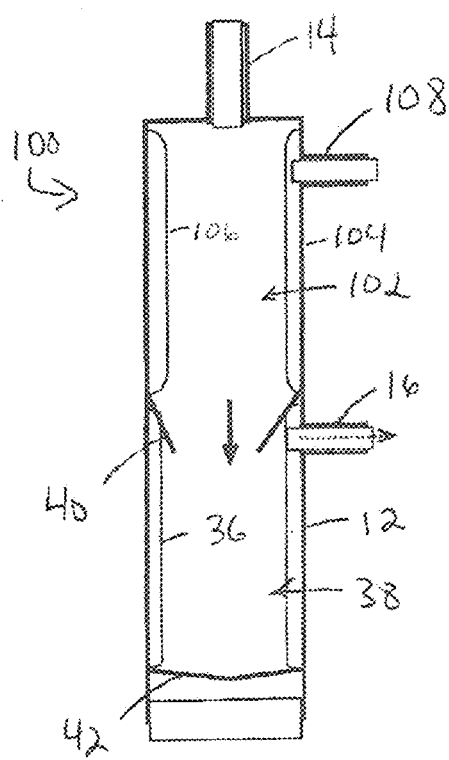
FIGS. 6a and 6b show the heat exchanger including an atrium, in diastolic phase (FIG. 6a) and in systolic phase (FIGS. 6b)
Figure 6B:
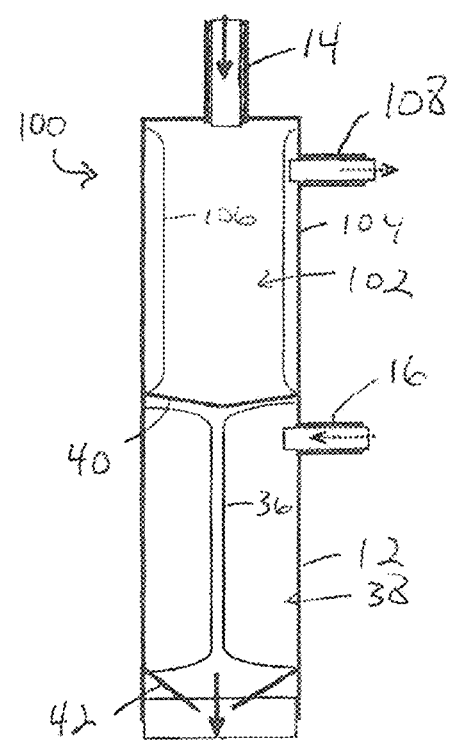

In another aspect, an atrium 100 is provided which further improves blood flow through the heat exchanger 10 of the present disclosure (see FIGS. 6a and 6b). In an embodiment, the atrium 100 is defined by at least one additional pneumatic pump 102, disposed at or defining the blood inlet of the heat exchanger 10. As shown the at least one additional pneumatic pump 102 is configured substantially as described above for the integral pneumatic pump 38 of the heat exchanger 10, including a pneumatic cylinder 104 and flexible membrane 106, and a gas inlet/outlet 108. For convenience and compactness, the atrium outlet valve may define the inlet valve 40 for the heat exchanger 10 integrated pneumatic pump 38, although of course the valve structures may be entirely separate.

The atrium 100 operates in systolic and diastolic phases as described for the heat exchanger 10 pneumatic pump 38. That is, cyclically supplying gas to the gas inlet/outlet 108 causes the atrium pneumatic pump 102 flexible membrane 106 to expand and collapse. passing blood through the pneumatic pump 102 and into the heat exchanger 10.

Figure 7:
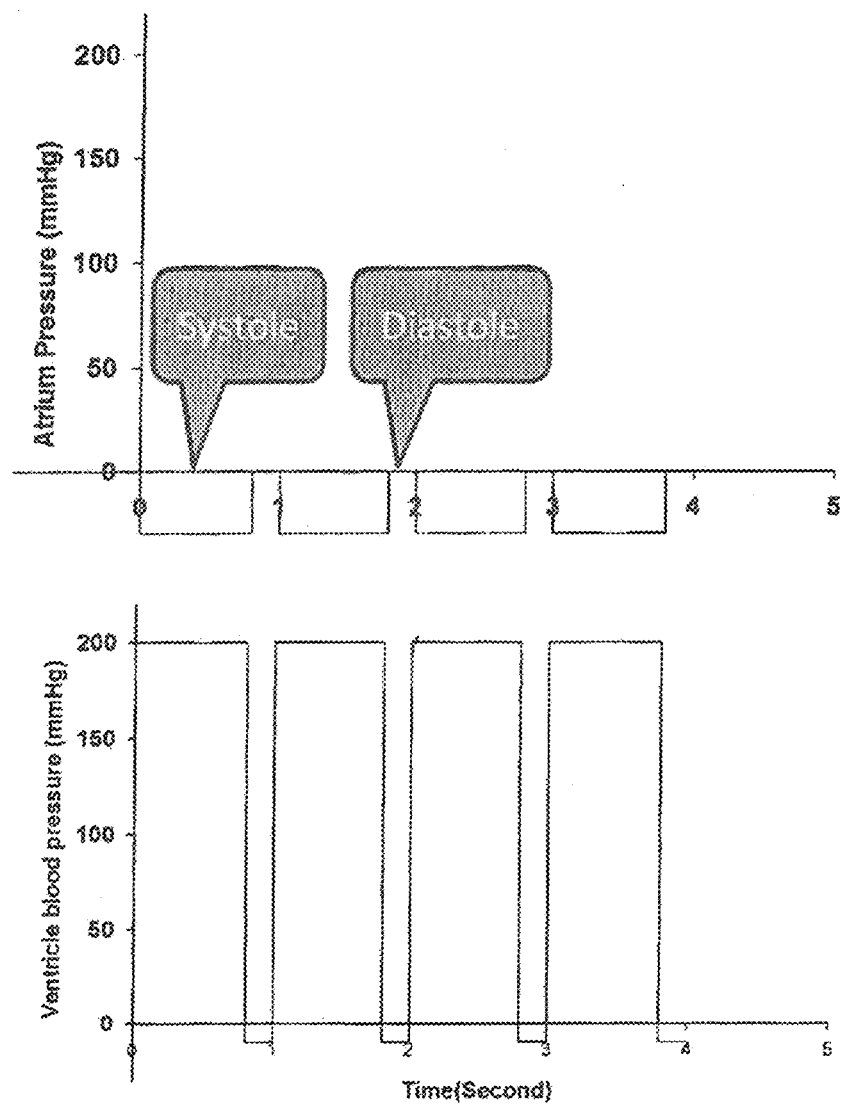
FIG. 7 graphically depicts relative internal pressures of the atrium and heat exchanger in systolic and diastolic phases.

In use, the atrium 100 is kept primarily in a state of negative internal pressure by withdrawal of gas, with the exception of a time immediately prior to the diastolic phase of the heat exchanger 10 pneumatic pump 38 (see FIG. 7). Typically, the atrium 100 internal pressure is substantially zero at the highest, i.e. during diastole. This is accomplished by intermittently discontinuing withdrawal of gas from the atrium 100 (as distinguished from affirmatively supplying gas to the atrium 100 pneumatic pump 102). In contrast, the heat exchanger 10 pneumatic pump 38 is provided only a very short phase of negative internal pump pressure (see FIG. 7). In diastole, when an internal pressure of the atrium 100 pneumatic pump 102 is highest, an internal pressure of the heat exchanger 10 pneumatic pump 38 is made slightly negative by withdrawal of gas (see FIG. 7).

By this design, the skilled artisan will appreciate that a consistent flow of blood is established into the inlet of the heat exchanger 10 compared to the pulsatile and irregular entry of blood into heat exchangers established by conventional designs. This is because the internal pressure of the atrium 100 into which blood first flows is almost always negative and blood is almost always draining from the patient and into the atrium. In turn, very little resistance is imposed to transfer of blood from the atrium 100 into the heat exchanger 10 to fill the pneumatic pump 38, since when pump gas is withdrawn from the heat exchanger 10 pneumatic pump 38 (diastole, see FIGS. 6a and 7), the internal pressure of the atrium 100 is zero at its highest, i.e. slightly higher than the internal pressure of the heat exchanger 10 pneumatic pump 38. By this mechanism, transfer of blood from the atrium 100 to the heat exchanger 10 pneumatic pump 38 is promoted by that slight pressure differential. These differentials are shown graphically in FIG. 7. Of course, the more even and non-pulsatile blood flow pattern established between the atrium 100 and the heat exchanger 10 achieved by the present mechanism should not be confused with the pulsatile flow established for blood passing through the heat exchanger 10 via the heat exchanger pneumatic pump 38, for the benefits described above.

The present heat exchanger 10 will typically be supplied with blood from a patient's body by a cannula. A dual lumen cannula such as those described in U.S. Pat. No. 7,473,239 and/or U.S. Published Patent Appl. No. US 2011/0040241 is preferred, which both passes blood from a patient's body via a withdrawal cannula into the oxygenator 10 and passes blood back into the patient's body via a delivery cannula. The dual lumen cannula may be inserted through a small incision into the right jugular vein, via the superior vena cava and traversing the right atrium, with the tip positioned in the inferior vena cava. This has the further advantage of reducing the length of the defined blood flow circuit and thereby the length of the vv-PISH circuit, reducing the length of time blood is exposed to potentially damaging heat and also the amount of heat required to raise the blood temperature to a desired level, and further eliminates multiple and potentially dangerous (to the patient)cannulations. In combination with the pump-integrated heat exchanger 10 of the present disclosure, use of a dual lumen cannula allows shortening the vv-PISH circuit to $\frac{1}{10}^{th}$ that of prior art systems. Blood contact surface area, circuit resistance, and circuit heat loss are significantly reduced, improving efficiency, reliability, and performance.

An electronically controlled pneumatic console may be provided to drive the above-described pneumatic pump 38. Because the pump-integrated heat exchanger 10 includes a. pneumatic pump 38 of lesser capacity than is needed to drive a conventional heat exchanger, a more compact pneumatic console is possible.

There is accordingly provided by the present disclosure a compact, efficient heat exchanger 10 which provides a pulsatile, evenly dispersed blood flow therethrough, augmenting heat exchange performance and in turn allowing a lessened heat exchange surface area providing a necessary level of heating of blood, to allow a more compact and efficient design. The heat exchanger 10 may include an atrium 100 defined by one or more additional pneumatic pumps 102, for regulating and providing an even blood supply from a patients'circulatory system into the heat exchanger 10. The heat exchanger 10 finds use in a variety of procedures, including supplementing conventional cancer chemotherapy regimens. Unlike conventional heat exchanger designs, the present heat exchanger 10 reduces or eliminates regions of stagnant or limited blood flow leading to thrombosis and device occlusion/failure, and further provides a pulsatile flow which also decreases stagnant blood flow and reduces thrombogenicity.

In turn, the integrated pump design of the heat exchanger 10 eliminates connectors and tubing such as are found in conventional heat exchanger/non-integral pump designs, reducing resistance to blood flow and improving pump performance. The combined integrated pump/heat exchanger lung design simplifies and shortens the vv-PISH circuit in that only one component is provided in the circuit, and further increases pump efficiency by eliminating blood flow resistance from connections between the pump and the artificial lung.

One of ordinary skill in the art will recognize that additional embodiments of the invention are also possible without departing from the teachings herein. For example, the above-described vv-PISH system may optionally include a dialysis unit (not shown) for use in patients with compromised kidney function. The dialysis unit may he connected via connectors (not shown) on the heat exchanger 10 blood inlet/outlet. Advantageously, the pressure gradient created by the heat exchanger 10 will drive up to 30% of the circuit blood flow (recirculation) through the dialysis unit, without requiring additional external pumps.

This detailed description, and particularly the specific details of the exemplary embodiments, is given primarily for clarity of understanding, and no unnecessary limitations are to be imported, for modifications will become obvious to those skilled in the art upon reading this disclosure and may be made without departing from the spirit or scope of the invention. Relatively apparent modifications, of course, include combining the various features of one or more figures or examples with the features of one or more of other figures or examples.

What is claimed is:

1. A compact heat exchanger for veno-venous perfusion-induced hyperthermia, comprising:
    a housing, a blood inlet ending at a distal-most surface of the compact heat exchanger and defining a longitudinal axis, a blood outlet, a heated fluid inlet, and a heated fluid outlet;
    a hollow tubule heat exchange array disposed within an interior of the housing for heat exchange to and from blood passing through the compact heat exchanger;
    an inlet blood flow redirector disposed at a distal-most end of the blood inlet and configured to redirect a flow of the blood radially to the longitudinal axis across the compact heat exchanger distal-most surface and therefrom to the hollow tubule heat exchange array, the blood perfusing therefrom to the blood outlet; and
    a pneumatic pump disposed substantially within the blood inlet and within a perimeter defined by the housing, further wherein the pneumatic pump is disposed in an interior of the hollow tubule heat exchange array.

2. The heat exchanger of claim 1, wherein the pneumatic pump provides a blood flow rate of from about 0.5 to about 2 L/minute.

3. The heat exchanger of claim 2, wherein a heat exchanging surface area of the hollow tubule heat exchange array is optimal for heating the blood passing therethrough at a flow rate of from about 0.5 to about 2 L/minute to a blood temperature of up to 44 C for delivery to a patient body.

4. The heat exchanger of claim 1, wherein the hollow tubule heat exchange array is fabricated of a suitable heat exchanging metal.

5. The heat exchanger of claim 4, wherein the suitable heat exchanging metal is stainless steel.

6. A veno-venous perfusion-induced hyperthermia system, comprising:
    a compact heat exchanger comprising:
        a housing, a blood inlet ending at a distal-most surface of the compact heat exchanger and defining a longitudinal axis, a blood outlet, a heated fluid inlet, and a heated fluid outlet;
        a hollow tubule heat exchange array disposed within an interior of the housing for heat exchange to and from blood passing through the compact heat exchanger;
        an inlet blood flow redirector disposed at a distal-most end of the blood inlet and configured to redirect a flow of the blood radially to the longitudinal axis across the compact heat exchanger distal-most surface and therefrom to the hollow tubule heat exchange array, the blood perfusing therefrom to the blood outlet; and
        a pneumatic pump disposed substantially within the blood inlet and within a perimeter defined by the housing, further wherein the pneumatic pump is disposed in an interior of the hollow tubule heat exchange array;
    a pneumatic console for cyclically supplying and withdrawing gas to and from the compact heat exchanger to operate the pneumatic pump and thereby pass the blood over the compact heat exchanger hollow tubule heat exchange array;
    another pump for passing heated fluid through the compact heat exchanger hollow tubule heat exchange array;
    and a dual lumen cannula for withdrawing the blood from a patient body, passing the blood through the compact heat exchanger, and returning the blood to the patient body.

7. The veno-venous perfusion-induced hyperthermia system of claim 6, wherein the pneumatic console and pneumatic pump provide a blood flow rate of from about 0.5 to about 2 L/minute.

8. The veno-venous perfusion-induced hyperthermia system of claim 7, wherein a heat exchanging surface area of the hollow tubule heat exchange array is optimal for heating the blood passing therethrough at a flow rate of from about 0.5 to about 2 L/minute to a blood temperature of up to 44 C for delivery to a patient body.

9. The veno-venous perfusion-induced hyperthermia system of claim 8, wherein the hollow tubule heat exchange array is fabricated of a suitable heat exchanging metal.

10. The veno-venous perfusion-induced hyperthermia system of claim 9, wherein the suitable heat exchanging metal is stainless steel.

11. A compact heat exchanger for veno-venous perfusion-induced hyperthermia, comprising:
    a housing, a blood inlet ending at a distal-most surface of the compact heat exchanger and defining a longitudinal axis, a blood outlet, a heated fluid inlet, and a heated fluid outlet;
    a hollow tubule heat exchange array disposed within an interior of the housing for heat exchange to and from blood passing through the compact heat exchanger;
    an inlet blood flow redirector disposed at a distal-most end of the blood inlet, the inlet blood flow redirector including a conical tip extending into an interior lumen of the distal-most end of the blood inlet for evenly dispersing the blood radially to the longitudinal axis across the compact heat exchanger distal-most surface and therefrom to the hollow tubule heat exchange array, the blood perfusing therefrom to the blood outlet; and
    a pneumatic pump disposed substantially within the blood inlet and within a perimeter defined by the housing, further wherein the pneumatic pump is disposed in an interior of the hollow tubule heat exchange array.

* * * * *